United States Patent [19]

Hecht

[11] 4,371,462

[45] Feb. 1, 1983

[54] METHOD FOR PURIFICATION OF ANTERIOR PITUITARY HORMONES

[75] Inventor: Randy I. Hecht, Rockville, Md.

[73] Assignee: Genex Corporation, Rockville, Md.

[21] Appl. No.: 341,216

[22] Filed: Jan. 21, 1982

[51] Int. Cl.³ .......................... A61K 35/55; C07G 7/00
[52] U.S. Cl. ................................. 260/112 R; 424/108
[58] Field of Search ..................... 260/112 R; 424/108

[56] References Cited

U.S. PATENT DOCUMENTS

| | | | |
|---|---|---|---|
| 3,098,792 | 7/1963 | Reisfeld et al. | 424/108 |
| 3,265,579 | 8/1966 | Daniels et al. | 167/74 |
| 3,275,515 | 9/1966 | DeVries | 424/108 |
| 3,503,950 | 3/1970 | Li | 424/108 X |
| 3,651,231 | 3/1972 | Epstein | 424/108 |
| 4,198,338 | 4/1980 | Treiber et al. | 260/326.31 |
| 4,332,717 | 6/1982 | Kanaoka et al. | 260/112 R |

OTHER PUBLICATIONS

J. of Biol. Chem. 211, pp. 555–558 (1954), Li.
Methods in Enzymology, vol. XXII, 1971, Jakoby, pp. 248–252.
Wallis et al., *Biochem. J.*, 100, pp. 593–599 (1966).
Muniz, et al., *Analytical Biochemistry*, 83, pp. 724–738 (1977).
Wilhelmi, *Handbook of Physiology-Endocrinology IV*, Part 2, "Chemistry of Growth Hormone," pp. 59–78.

*Primary Examiner*—Howard E. Schain
*Attorney, Agent, or Firm*—Bernard, Rothwell & Brown

[57] ABSTRACT

Mixtures containing an anterior pituitary hormone such as growth hormone or prolactin are treated to produce relatively pure hormone by a process comprising eluting the mixture through an ion-exchange column followed by fractionation of the eluent on an isoelectric focusing column. Fractions at the isoelectric point of the specific anterior pituitary hormone can be pooled, dialyzed with sterile water, and then lyophilized. The identity of the resulting product can be confirmed by electrophoretic analysis on sodium dodecylsulfate gel, immunodiffusion on an Ouchterlony plate, or both.

23 Claims, No Drawings

METHOD FOR PURIFICATION OF ANTERIOR PITUITARY HORMONES

This invention relates to purification of proteins. More particularly this invention relates to the purification of anterior pituitary hormones such as growth hormones or prolactins.

Anterior-pituitary hormones are obtained from the anterior lobe of the vertebrate pituitary gland, i.e., the adenohypophysis. These hormones are all proteins and can be classified as either gonadotropic or metabolic hormones on the basis of biological studies. Included among these hormones are the growth hormones and prolactins.

Growth hormones are anabolic proteins produced by the anterior pituitary gland of vertebrates. Their molecular weights are approximately 22,000 daltons. These hormones promote the growth of tissues and are involved in regulating other phases of protein metabolism as well as fat, carbohydrate and mineral metabolism. Growth hormone produced in animals of different species vary in antigens induced, isoelectric points, N-terminal and C-terminal amino acid residues, and amino acid composition. Growth hormones are generally species-specific, that is, growth hormone from one species is inactive in another species.

A variety of disorders can be attributed to growth hormone deficiency in animals. Foremost among these in humans is pituitary dwarfism. Administration of growth hormone can overcome pituitary deficiency. Furthermore, growth hormone is useful in the treatement of gastrointestinal bleeding, promoting the healing of bone fractures and accelerating the healing of contusions and other wounds. Growth hormones are also valuable in the raising of livestock when used as dietary supplements to promote meat and milk production without increased feed consumption.

Growth hormones can be obtained by isolation from excised pituitary tissue. See, e.g., C. H. Li, *J. Biol. Chem.* 211, 55 (1954). Growth hormones can also be obtained from genetically engineered microorganisms containing recombinant DNA which specifies the production of growth hormone. See, P. H. Seeburg, et al., *Nature*, 276, 795–798 (1978); P. H. Seeburg et al., *Nature*, 270, 486–494 (1978); J. A. Martial, *Science*, 205, 602–607 (1979).

Both of these methods require separation of growth hormone from a pituitary homogenate or a fermentation medium which contains biological contaminants. These contaminants tend to reduce the specific biological activity of growth hormone as well as possibly causing unwanted side effects, e.g., undesired immunological responses.

Prolactin, also known as lactogenic hormone, has been isolated from both sheep and ox pituitaries. Prolactins are proteins consisting of a single polypeptide chain with threonine at the N-terminus. The C-terminus is occupied by a half cystine residue forming a loop with the rest of the molecule through a disulfide bond. The prolactins are instrumental in inducing lactation in mammals at parturition, mammary gland proliferation, and releasing progesterone from leutin cells.

The process of the present invention relates to a method for recovering anterior pituitary hormones such as growth hormone or prolactin, substantially free of contaminants from pituitary homogenates or fermentation media which contain anterior pituitary hormone-producing microorganisms. This is achieved by passing the hormone containing mixture over an ion-exchange column and fractionating the eluate on an isoelectric focusing column. Fractions of the eluate are collected from the isoelectric focusing column at or near the isoelectric pH of the particular hormone in question. For example, human growth hormone would be collected from the isoelectric focusing column at a pH of 4.9, while sheep growth hormone would be collected at its isoelectric point of 6.8. The isoelectrically focused fractions are advantageously collected and dialyzed against sterile water, and the resulting dialysis product can then be freeze-dried. The identity of the lyophilized product can be confirmed by electrophoretic analysis on sodium dodecylsulfate gel, immunodiffusion on an Ouchterlony plate, or both.

Substantially pure anterior pituitary hormones can be obtained from the anterior pituitary gland of vertebrates by homogenizing pituitaries in a buffer solution containing salt.

Homogenization is carried out in an ionizable salt-containing buffer whose composition, pH and ionic strength are not deleterious to the hormone. The buffer preferably contains sufficient salt to effect a crude fractionation by salting-out contaminating proteins, yet insufficient salt to cause precipitation of the desired hormone. The composition of such buffer can vary widely. Generally the buffer has a pH ranging from about 7–9 and an ionic strength equivalent to about a 0.1 to 1 molar NaCl solution. See, e.g., Wallis et al., *Biochem. J.*, 100: 593–599 (1966).

After the anterior pituitaries are homogenized, the resulting homogenate is dialyzed against a buffer solution similar to the above-described buffer except that it lacks the highly ionizable salt. This dialysis is undertaken to lower the ionic strength of the homogenate solution. Removal of the ions prevents ionic interference with subsequently contacted ion-exchange chromotography materials and avoids the deleterious effects resulting from contact of the hormone with a solution of high ionic strength.

Upon completion of dialysis, the dialyzed fraction containing growth hormone is further purified by ion-exchange chromatography. Conventional methods of purification rely upon hormones of impure hormone-containing solutions binding to the column. See, *Methods in Enzymology* Vol. XXII, Section 4, Ed. W. B. Jakoby, Academic Press, N.Y. (1971). The impurities of the solution pass through the column and are collected in the eluate. Additional steps of deactivating the column and collecting the bound hormone are generally required.

It has now been discovered that, unlike most hormones, anterior pituitary hormones such as growth hormones or prolactins pass unhindered through anion-exchange columns. This property permits continuous purification of anterior pituitary hormone-containing mixtures on an anion-exchange column. The desired hormone passes through the column while a substantial portion of the impurities remain behind, entrapped within the column. Such a procedure does not require constant deactivation of the column and removal of the hormone therefrom. Instead, the anion-exchange purification can continue uninterrupted, limited only by the capacity of the column to retain impurities. Upon this capacity being reached, the column can be deactivated, the impurities eluted, and the procedure begun anew.

Anion exchange materials such as diethylaminocellulose, (e.g., DE-52 available from Whatman Chemical Separations, Inc., Clifton, N.J.), have been found to be suitable in the process of the present invention. The buffer used for eluting the dialysate through the anion-exchange column is generally similar to the homogenization buffer, except that the salt content is preferably substantially reduced.

The dialyzed homogenate is passed through the activated anion-exchange column and the anterior pituitary hormone is collected in the eluate. The eluate is then concentrated by ultrafiltration utilizing an ultrafiltration membrane having a molecular weight cutoff of about 10,000.

Because the ultrafiltration procedure causes an increase in ionic strength of the anterior pituitary hormone-containing solution, the concentrated filtrate is dialyzed against sterile water so as to reduce ionic strength.

The resulting hormone-containing dialysis product is further purified by the process of isoelectric focusing in which an electrochemically induced pH gradient is developed at constant temperature in a vertical column between an anode and a cathode. Such a gradient is composed of low molecular weight polymers of amino acids of various charges and pH's known as ampholytes which establish a pH gradient in response to the difference in potential between the anode and cathode. Ampholyte mixtures of various pH ranges are commercially available (e.g., from LKB, Rockville, MD), and the particular pH range employed will depend upon the isoelectric point of the protein of interest.

The pH gradient is advantageously stabilized within a sucrose density gradient. Mixtures of protein which are added to the column migrate toward the anode or cathode until they reach the pH of their isoelectric or "focusing" point. Separation of proteins which differ by as little as 0.01 pH unit can be accomplished using this technique. The process of the present invention can utilize an LKB 440 ml preparative isoelectric focusing column available from LKB, Rockville, MD.

As the protein components are eluted from the column, their absorbance is measured by ultraviolet spectrophotometry at $A_{280}$ (280 nm). The pH is taken of consecutive 1.0 ml fractions of the eluate. The fractions within about 0.3 and preferably within about 0.1 pH unit of the isoelectric point of the particular anterior pituitary hormone under consideration are then pooled to form active fractions. Table I lists the isoelectric points of various anterior pituitary hormones.

Because isoelectrically focused materials can contain various impurities such as ampholytes, sucrose, and urea, the pooled fractions are preferably dialyzed against sterile water and dried, e.g., lyophilized, to yield the purified anterior pituitary hormone material.

Alternatively, the pooled fractions can be purified on a Sephadex column which retains compounds having a molecular weight of 10,000 or above. The material retained on the column can then be removed and dried. The identity of the purified protein can be confirmed by electrophoretic analysis of samples on a sodium dodecyl sulfate gel electrophoresis (see Weher, K., et al., *J. Biol. Chem.* 224, 4406 (1968)), as well as an Ouchterlony plate (see Garvey, J. S. et al., *Methods in Immunology* Vol. III, W. A. Benjamin, Inc., Massachusetts (1977) pp. 313–321)).

The process of the present invention can also be used to purify anterior pituitary hormones which are produced by microorganisms. Substantially the same procedure is followed unless the hormones produced remain intracellular. In such cases, the cells can be lysed to release the hormones during homogenization.

The following examples set forth how to perform the process of the invention; however, these examples are not in any way to be construed as limiting.

EXAMPLE I

Purification Procedure of Bovine Growth Hormone Obtained from Pituitaries

Fifty bovine pituitaries, weighing 101 grams, were homogenized in a Virtis 45 homogenizer using 200 ml of 0.25 M NaCl in borate-HCl, pH 8.7, buffer solution. This homogenate was then allowed to stir for three hours in an ice bath. The homogenate was subsequently spun down in a Sorval ® centrifuge at 5000 rpm for 15 minutes and the supernatant decanted.

The decanted supernatant was dialyzed against a buffer solution containing a borate-HCl, pH. 8.7 buffer, free of NaCl. The dialysis product was then run through a DEAE-52 column (30 cm×7 cm). The BGH passing through the DEAE column was collected and concentrated by ultrafiltration on an Amicon ® apparatus, and then placed on a preparative isoelectric focusing column (pH range, 6.0–8.0). After 40 hours, elution started from the column and fractions at pH 6.8 were collected, pooled and dialyzed against sterile $H_2O$. The BGH-containing solution was again ultrafiltered using an Amicon ® apparatus. The yield of pure BGH was approximately 85 mg.

At every step of the purification procedure, SDS-gel electrophoresis, Ouchterlony immunoassays and Bio-Rad protein assays were performed to monitor the purity of the resulting products.

EXAMPLE II

Purification Procedure of Human Growth Hormone Obtained from Genetically Modified *E. Coli*

Genetically modified *E. coli* cells capable of producing human growth hormone are made according to the method described in European Patent Application No. 002,0141 to Baxter et al. The *E. coli* cells are cultivated in a fermentation medium and human growth hormone is released by dialyzing the cells with a lysozyme. The resulting mixture is then buffered with 200 ml of 0.25 M NaCl in borate-HCl, pH 8.7 buffer solution. The resulting mixture is then allowed to stir for three hours in an ice bath. The homogenate is subsequently spun down in a Sorval ® centrifuge at 5000 rpm for 15 minutes and the supernatant decanted.

The decanted supernatant dialyzed against a buffer solution containing borate-HCl, pH 8.7 buffer, free of NaCl. The dialysis product is then run through a DEAE-52 column (30 cm×7 cm). The growth hormone passing through the DEAE column is collected and concentrated by ultrafiltration on an Amicon ® apparatus, and then placed on a preparative isoelectric focusing column (pH range, 6.0–8.0). After 40 hours, elution starts from the column and fractions at pH 4.9 are collected, pooled and dialyzed against sterile $H_2O$. The growth hormone containing solution is again ultrafiltered using an Amicon ® apparatus to yield pure human growth hormone.

At every step of the purification procedure, SDS-gel electrophoresis, Ouchterlony immunoassays and Bio- Rad protein assays are performed to monitor the purity of the resulting products.

TABLE I

Isoelectric Points of Anterior-Pituitary hormones

| Hormone | Isoelectric Point |
| --- | --- |
| GH (human) | 4.9 |
| GH (monkey) | 5.5 |
| GH (whale) | 6.2 |
| GH (pig) | 6.3 |
| GH (sheep) | 6.8 |
| GH (beef) | 6.8 |
| Prolactin (sheep) | 5.7 |
| Prolactin (beef) | 5.7 |

It is claimed:

1. A process of purifying anterior pituitary hormone which comprises eluting an anterior pituitary hormone-containing mixture on an anion-exchange column with a buffer solution, separating the eluate on an isoelectric focusing column, and retaining the fractions collected at or near the isoelectric point of the anterior pituitary hormone.

2. The process of claim 1 wherein the fractions collected at or near the isoelectric point of the anterior pituitary hormone are dialyzed with sterile water and then lyophilized.

3. The process of claim 2 wherein the lyophilized fractions are generated out on sodium dodecylsulfate gel and an Ouchterlony plate.

4. The process of claim 1, 2, or 3 wherein the anterior pituitary hormone purified is growth hormone.

5. The process of claim 1, 2, or 3 wherein the growth hormone purified is bovine growth hormone.

6. The process of claim 4 wherein the growth hormone purified is human growth hormone.

7. The process of claim 4 wherein the growth hormone purified is porcine growth hormone.

8. The process of claim 4 wherein the growth hormone purified is ovine growth hormone.

9. The process of claim 4 wherein the growth hormone purified is rat growth hormone.

10. The process of claim 4 wherein the growth hormone purified is ox growth hormone.

11. The process of claim 1, 2, or 3 wherein the anterior pituitary hormone purified is prolactin.

12. The process of claim 11 wherein the prolactin is bovine prolactin.

13. The process of claim 11 wherein the prolactin is human prolactin.

14. The process of claim 11 wherein the prolactin is porcine prolactin.

15. The process of claim 11 wherein the prolactin is ovine prolactin.

16. The process of claim 11 wherein the prolactin is rat prolactin.

17. The process of claim 11 wherein the prolactin is ox prolactin.

18. The process of claim 1 wherein the anterior pituitary hormone-containing mixture is obtained by homogenizing pituitaries in a buffer solution having a pH ranging from about 7 to 9 and an ionic strength equivalent to about a 0.1 to 1 molar NaCl solution.

19. The process of claim 18 wherein the buffer is 0.25 M NaCl in borate-HCl and has a pH of about 8.7.

20. The process of claim 1 wherein a borate-HCl buffer solution having a pH ranging from 7 to 9 is used to elute the anterior pituitary hormone-containing mixture on an anion-exchange column.

21. The process of claim 20 wherein the buffer solution eluent has a pH of about 8.7.

22. A process of purifying anterior pituitary hormone which comprises lowering the ionic strength of a hormone-containing homogenate by dialysis, purifying the dialysis product by eluting it through an anion-exchange chromotographic column, concentrating the eluate by ultrafiltration, reducing the ionic strength of the ultrafiltrate by dialyzing it against sterile water, separating the dialyzed ultrafiltrate on an isoelectric focusing column and retaining the fractions collected at or near the isoelectric point.

23. The process of claim 22 wherein the eluate is concentrated by an ultrafiltration membrane having a molecular weight cutoff of about 10,000.

* * * * *

UNITED STATES PATENT AND TRADEMARK OFFICE
CERTIFICATE OF CORRECTION

PATENT NO. : 4,371,462

DATED : February 1, 1983

INVENTOR(S) : Randy I. Hecht

It is certified that error appears in the above-identified patent and that said Letters Patent is hereby corrected as shown below:

Claim 3, line 2, "generated" should be --separated--.

Signed and Sealed this

Fifth Day of April 1983

[SEAL]

Attest:

GERALD J. MOSSINGHOFF

Attesting Officer

Commissioner of Patents and Trademarks